(12) United States Patent
Jennings

(10) Patent No.: US 8,845,594 B2
(45) Date of Patent: Sep. 30, 2014

(54) AUTO-INJECTOR WITH FILLING MEANS

(75) Inventor: Douglas Ivan Jennings, Royston (GB)

(73) Assignee: Cilag GmbH International, Zug (CH)

( * ) Notice: Subject to any disclaimer, the term of this patent is extended or adjusted under 35 U.S.C. 154(b) by 39 days.

(21) Appl. No.: 12/997,598

(22) PCT Filed: Jun. 10, 2009

(86) PCT No.: PCT/GB2009/001451
§ 371 (c)(1),
(2), (4) Date: Dec. 12, 2010

(87) PCT Pub. No.: WO2009/153544
PCT Pub. Date: Dec. 23, 2009

(65) Prior Publication Data
US 2011/0098647 A1    Apr. 28, 2011

(30) Foreign Application Priority Data
Jun. 19, 2008  (GB) .................................. 0811347.4

(51) Int. Cl.
*A61M 5/32* (2006.01)
*A61M 5/00* (2006.01)
*A61M 5/20* (2006.01)
*A61M 5/178* (2006.01)

(52) U.S. Cl.
CPC ....... *A61M 5/2033* (2013.01); *A61M 2005/208* (2013.01); *A61M 5/1782* (2013.01); *A61M 2005/206* (2013.01); *A61M 5/326* (2013.01); *A61M 5/3204* (2013.01); *A61M 5/3287* (2013.01); *A61M 5/3202* (2013.01)
USPC .......................................... 604/197; 604/232

(58) Field of Classification Search
USPC ................................. 604/131, 154
See application file for complete search history.

(56) References Cited

U.S. PATENT DOCUMENTS

| 1,845,036 A | 2/1932 | Busher |
| 2,019,382 A | 10/1935 | Aronson |

(Continued)

FOREIGN PATENT DOCUMENTS

| CH | 518102 A | 1/1972 |
| CN | 2059579 U | 7/1990 |

(Continued)

OTHER PUBLICATIONS

International Search Report dated Sep. 5,2005; International Application No. PCT/GB2005/002117.

(Continued)

*Primary Examiner* — Aarti B Berdichevsky

(57) ABSTRACT

An injection device comprises a housing adapted to receive a fluid container having a discharge nozzle and a dispensing piston moveable in the fluid container to expel the contents of the fluid container out of the discharge nozzle. A drive is adapted on activation to act on the fluid container to advance it from a retracted position in which the discharge nozzle is contained within the housing to an extended position in which the discharge nozzle extends from the housing and act on the dispensing piston to expel the contents of the fluid container out of the discharge nozzle. A connector is adapted to receive a vial containing fluid and connect it to the discharge nozzle. There is also means to move the dispensing piston relative to the fluid container from a first position in which the dispensing piston is located in the fluid container adjacent the discharge nozzle to a second position in which the dispensing piston has been drawn away from the discharge nozzle, thereby drawing fluid from the vial into the fluid container.

15 Claims, 6 Drawing Sheets

(56) References Cited

U.S. PATENT DOCUMENTS

| | | |
|---|---|---|
| 2,531,267 A | 11/1950 | Harisch |
| 2,764,977 A | 10/1956 | Ferguson |
| 2,828,742 A | 4/1958 | Ashkenaz |
| 3,320,955 A | 5/1967 | Sarnoff |
| 3,329,146 A | 7/1967 | Waldman |
| 3,543,603 A | 12/1970 | Gley |
| 3,656,472 A | 4/1972 | Ben Moura |
| 3,702,608 A | 11/1972 | Tibbs |
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 3,976,069 A | 8/1976 | Ong |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,222,380 A | 9/1980 | Terayama |
| 4,231,368 A | 11/1980 | Becker |
| 4,236,516 A | 12/1980 | Nilson |
| 4,299,238 A | 11/1981 | Baidwan et al. |
| 4,378,015 A | 3/1983 | Wardlaw |
| 4,394,863 A | 7/1983 | Bartner |
| 4,403,989 A | 9/1983 | Christensen et al. |
| 4,407,283 A | 10/1983 | Reynolds |
| 4,425,120 A | 1/1984 | Sampson et al. |
| 4,430,082 A | 2/1984 | Schwabacher |
| 4,521,237 A | 6/1985 | Logothetis |
| 4,561,856 A | 12/1985 | Cochran |
| 4,636,201 A | 1/1987 | Ambrose et al. |
| 4,639,250 A | 1/1987 | Rycroft |
| 4,642,099 A | 2/1987 | Phillips et al. |
| 4,676,530 A | 6/1987 | Nordgren et al. |
| 4,744,786 A | 5/1988 | Hooven et al. |
| 4,787,891 A | 11/1988 | Levin et al. |
| 4,874,383 A | 10/1989 | McNaughton |
| 4,874,384 A | 10/1989 | Nunez |
| 4,929,232 A | 5/1990 | Sweeney et al. |
| 4,969,870 A | 11/1990 | Kramer et al. |
| 4,988,339 A | 1/1991 | Vadher |
| 5,009,646 A | 4/1991 | Sudo et al. |
| 5,026,349 A | 6/1991 | Schmitz et al. |
| 5,057,079 A | 10/1991 | Tiemann et al. |
| 5,092,842 A | 3/1992 | Bechtold et al. |
| 5,098,400 A | 3/1992 | Crouse et al. |
| 5,112,119 A | 5/1992 | Cooke et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,147,325 A | 9/1992 | Mitchell et al. |
| 5,156,599 A | 10/1992 | Ranford et al. |
| 5,176,643 A | 1/1993 | Kramer et al. |
| 5,190,526 A | 3/1993 | Murray et al. |
| 5,242,416 A | 9/1993 | Hutson |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,312,364 A | 5/1994 | Jacobs |
| 5,330,081 A | 7/1994 | Davenport |
| 5,330,430 A | 7/1994 | Sullivan |
| 5,358,489 A | 10/1994 | Wyrick |
| 5,364,369 A | 11/1994 | Reynolds |
| 5,368,577 A | 11/1994 | Teoh et al. |
| 5,372,586 A | 12/1994 | Haber et al. |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,503,627 A | 4/1996 | McKinnon et al. |
| 5,514,097 A | 5/1996 | Knauer |
| 5,520,653 A | 5/1996 | Reilly et al. |
| 5,540,660 A | 7/1996 | Jenson et al. |
| 5,540,666 A | 7/1996 | Barta et al. |
| 5,540,709 A | 7/1996 | Ramel et al. |
| 5,567,160 A | 10/1996 | Massino |
| 5,569,191 A | 10/1996 | Meyer |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,607,395 A | 3/1997 | Ragsdale et al. |
| 5,609,577 A | 3/1997 | Haber et al. |
| 5,609,584 A | 3/1997 | Gettig et al. |
| 5,611,785 A | 3/1997 | Mito et al. |
| 5,637,094 A | 6/1997 | Stewart, Jr. et al. |
| 5,645,536 A | 7/1997 | Whisson |
| 5,647,845 A | 7/1997 | Haber et al. |
| 5,658,259 A | 8/1997 | Pearson et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A | 1/1998 | Olive et al. |
| 5,713,866 A | 2/1998 | Wilmot |
| 5,748,316 A | 5/1998 | Wakabayashi et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,827,262 A | 10/1998 | Neftel et al. |
| 5,843,036 A | 12/1998 | Olive et al. |
| 5,855,839 A | 1/1999 | Brunel |
| 5,865,795 A | 2/1999 | Schiff et al. |
| 5,865,804 A | 2/1999 | Bachynsky |
| 5,868,711 A | 2/1999 | Kramer et al. |
| 5,879,327 A | 3/1999 | Moreau DeFarges |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |
| 5,997,513 A | 12/1999 | Smith et al. |
| 6,007,515 A | 12/1999 | Epstein et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross |
| 6,123,684 A | 9/2000 | Deboer et al. |
| 6,139,534 A | 10/2000 | Niedospial, Jr. et al. |
| 6,159,161 A | 12/2000 | Hodosh |
| 6,159,181 A | 12/2000 | Crossman et al. |
| 6,159,184 A | 12/2000 | Perez et al. |
| 6,162,199 A | 12/2000 | Geringer |
| 6,171,276 B1 | 1/2001 | Markus et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart, Sr. |
| 6,209,738 B1 | 4/2001 | Jansen et al. |
| 6,221,044 B1 | 4/2001 | Grecco |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |

(56) References Cited

U.S. PATENT DOCUMENTS

| | | |
|---|---|---|
| 6,290,683 B1 | 9/2001 | Erez et al. |
| 6,293,925 B1 | 9/2001 | Safabash et al. |
| 6,317,939 B1 | 11/2001 | Malin |
| 6,330,960 B1 | 12/2001 | Faughey et al. |
| 6,332,875 B2 | 12/2001 | Inkpen et al. |
| 6,371,939 B2 | 4/2002 | Bergens et al. |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Aichas et al. |
| 6,569,124 B1 | 5/2003 | Perouse |
| 6,572,581 B1 | 6/2003 | Landua |
| 6,575,939 B1 | 6/2003 | Brunel |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,599,272 B1 | 7/2003 | Hjertman et al. |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landua |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau et al. |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,767,336 B1 | 7/2004 | Kaplan |
| 6,770,056 B2 | 8/2004 | Price et al. |
| 6,776,777 B2 | 8/2004 | Barelle |
| 6,783,509 B1 | 8/2004 | Landau et al. |
| 6,793,161 B1 | 9/2004 | Fujia et al. |
| 6,796,967 B2 | 9/2004 | Jensen |
| 6,811,548 B2 | 11/2004 | Jeffrey |
| 6,846,303 B2 | 1/2005 | Eakins et al. |
| 6,875,205 B2 * | 4/2005 | Leinsing ............ 604/414 |
| 6,890,319 B1 | 5/2005 | Crocker |
| 6,899,698 B2 | 5/2005 | Sams |
| 6,932,793 B1 | 8/2005 | Marshall et al. |
| 6,939,319 B1 | 9/2005 | Anstead et al. |
| 6,979,316 B1 | 12/2005 | Rubin et al. |
| 7,066,907 B2 | 6/2006 | Crossman et al. |
| 7,097,071 B2 | 8/2006 | Anderson et al. |
| 7,097,634 B2 | 8/2006 | Gilbert |
| 7,118,553 B2 | 10/2006 | Scherer |
| 7,156,823 B2 | 1/2007 | Landau et al. |
| 7,160,913 B2 | 1/2007 | Schneider |
| 7,294,122 B2 | 11/2007 | Kubo et al. |
| 7,354,427 B2 | 4/2008 | Fangrow |
| RE40,428 E | 7/2008 | Keane et al. |
| 7,442,185 B2 | 10/2008 | Amark et al. |
| 7,470,258 B2 | 12/2008 | Barker et al. |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,396 B2 * | 11/2009 | Slate et al. ............ 604/136 |
| 7,635,356 B2 | 12/2009 | Stamp |
| 7,645,271 B2 | 1/2010 | Fangrow |
| 7,654,995 B2 | 2/2010 | Warren et al. |
| 7,658,733 B2 | 2/2010 | Fangrow |
| 7,678,333 B2 | 3/2010 | Reynolds et al. |
| 7,682,345 B2 | 3/2010 | Savage |
| 7,717,879 B2 | 5/2010 | Mansouri |
| 7,744,561 B2 | 6/2010 | Stamp |
| 7,759,654 B2 | 7/2010 | Yan et al. |
| 7,794,434 B2 * | 9/2010 | Mounce et al. ............ 604/216 |
| 7,799,009 B2 | 9/2010 | Niedospial, Jr. et al. |
| 7,811,262 B2 * | 10/2010 | Moberg et al. ............ 604/201 |
| 7,828,764 B2 * | 11/2010 | Moberg et al. ............ 604/86 |
| 7,871,397 B2 | 1/2011 | Schraga |
| 7,879,010 B2 | 2/2011 | Hunn et al. |
| 7,883,499 B2 | 2/2011 | Fangrow |
| 7,959,715 B2 * | 6/2011 | Kavazov et al. ............ 96/6 |
| 7,972,321 B2 | 7/2011 | Fangrow |
| 8,100,154 B2 | 1/2012 | Reynolds et al. |
| 8,177,768 B2 * | 5/2012 | Leinsing ............ 604/411 |
| 8,277,414 B2 | 10/2012 | Barrow-Williams et al. |
| 8,313,463 B2 | 11/2012 | Barrow-Williams et al. |
| 8,409,138 B2 | 4/2013 | James et al. |
| 8,491,530 B2 | 7/2013 | Maritan |
| 2001/0005781 A1 | 6/2001 | Bergens et al. |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0109833 A1 | 6/2003 | Sahpe |
| 2003/0120212 A1 | 6/2003 | Dedig et al. |
| 2003/0120222 A1 | 6/2003 | Vaillancourt |
| 2003/0121815 A1 | 7/2003 | Bergeron |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La serna |
| 2003/0236502 A1 | 12/2003 | De La Serna |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |

(56) References Cited

U.S. PATENT DOCUMENTS

| | | |
|---|---|---|
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0020980 A1* | 1/2005 | Inoue et al. ............... 604/152 |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178631 A1 | 8/2006 | Gillespie et al. |
| 2006/0178642 A1 | 8/2006 | Gillespie et al. |
| 2006/0184119 A1* | 8/2006 | Remde et al. ............... 604/151 |
| 2006/0184137 A1 | 8/2006 | Reynolds |
| 2006/0189938 A1 | 8/2006 | Hommann et al. |
| 2006/0200093 A1* | 9/2006 | Lopez ............... 604/249 |
| 2006/0206060 A1* | 9/2006 | Lopez ............... 604/246 |
| 2006/0224124 A1 | 10/2006 | Scherer |
| 2006/0229572 A1* | 10/2006 | Lopez ............... 604/256 |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0066939 A1* | 3/2007 | Krulevitch et al. ............ 604/152 |
| 2007/0078382 A1 | 4/2007 | Hommann et al. |
| 2007/0142787 A1 | 6/2007 | Scherer |
| 2007/0156091 A1 | 7/2007 | Fathallah et al. |
| 2007/0156112 A1* | 7/2007 | Walsh ............... 604/415 |
| 2007/0208296 A1* | 9/2007 | Paproski et al. ............... 604/82 |
| 2008/0033395 A1 | 2/2008 | Alchas |
| 2008/0172024 A1* | 7/2008 | Yow ............... 604/411 |
| 2008/0213590 A1 | 9/2008 | Greiner et al. |
| 2008/0269680 A1* | 10/2008 | Ibranyan et al. ............... 604/122 |
| 2008/0306443 A1* | 12/2008 | Neer et al. ............... 604/121 |
| 2008/0312602 A1 | 12/2008 | Barrow-Williams et al. |
| 2008/0312606 A1 | 12/2008 | Harrison et al. |
| 2009/0036764 A1* | 2/2009 | Rivas et al. ............... 600/365 |
| 2009/0054849 A1 | 2/2009 | Burnell et al. |
| 2009/0088688 A1 | 4/2009 | Timothy Donald |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2011/0092954 A1 | 4/2011 | Jennings |
| 2011/0098647 A1 | 4/2011 | Jennings |
| 2011/0098655 A1 | 4/2011 | Jennings et al. |
| 2011/0130743 A1 | 6/2011 | Jennings et al. |
| 2011/0282278 A1 | 11/2011 | Stamp et al. |
| 2012/0232491 A1 | 9/2012 | Jennings |
| 2012/0323177 A1 | 12/2012 | Adams et al. |
| 2013/0096512 A1 | 4/2013 | Ekman et al. |
| 2013/0267898 A1 | 10/2013 | Hourmand et al. |
| 2013/0317446 A1 | 11/2013 | Hourmand et al. |
| 2013/0331794 A1 | 12/2013 | Ekman et al. |
| 2013/0338601 A1 | 12/2013 | Cowe |
| 2013/0345643 A1 | 12/2013 | Hourmand et al. |

FOREIGN PATENT DOCUMENTS

| | | |
|---|---|---|
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 902776 C | 1/1954 |
| DE | 229932 A1 | 11/1985 |
| DE | 4428467 A1 | 2/1996 |
| DE | 29513214 U1 | 1/1997 |
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0515473 B1 | 12/1992 |
| EP | 0518416 A1 | 12/1992 |
| EP | 0331452 A2 | 8/1993 |
| EP | 0585626 A1 | 3/1994 |
| EP | 0389938 B1 | 5/1994 |
| EP | 0516473 B1 | 2/1996 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1755710 A1 | 2/2007 |
| EP | 1586341 B1 | 1/2008 |
| EP | 1932558 A1 | 6/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| FR | 1014881 A | 8/1952 |

(56) References Cited

FOREIGN PATENT DOCUMENTS

| | | |
|---|---|---|
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 | 5/1920 |
| GB | 0412054 | 6/1934 |
| GB | 728248 | 4/1955 |
| GB | 909898 | 11/1962 |
| GB | 1263355 | 2/1972 |
| GB | 1311937 A | 3/1973 |
| GB | 1514725 | 6/1978 |
| GB | 2338033 A | 12/1999 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2445090 A | 6/2008 |
| GB | 2446778 A | 8/2008 |
| GB | 2451663 A | 2/2009 |
| JP | 59-115053 A | 7/1984 |
| JP | 2-185261 A | 7/1990 |
| JP | 2-502971 T | 9/1990 |
| JP | H 02-299660 A | 12/1990 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | H 07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-212237 A | 8/2001 |
| JP | 2002-500933 T | 1/2002 |
| JP | 2002-502296 A | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-532500 T | 11/2003 |
| JP | 2003-533288 A | 11/2003 |
| JP | 2004-533282 T | 11/2004 |
| JP | 2004-537376 A | 12/2004 |
| JP | 2005-508214 A | 3/2005 |
| JP | 2005-177503 A | 7/2005 |
| JP | 2004-33737 A | 8/2005 |
| JP | 2006-223858 A | 8/2006 |
| JP | 2008-284177 A | 11/2008 |
| NZ | 335985 A | 4/2001 |
| NZ | 573171 A | 11/2010 |
| NZ | 573350 A | 12/2010 |
| WO | WO 88/08725 | 11/1988 |
| WO | WO 88/10129 A1 | 12/1988 |
| WO | WO 92/19296 A | 11/1992 |
| WO | WO 93/02186 A1 | 2/1993 |
| WO | WO 93/21986 A2 | 11/1993 |
| WO | WO 93/23098 A1 | 11/1993 |
| WO | WO 94/04207 A1 | 3/1994 |
| WO | WO 94/07554 A1 | 4/1994 |
| WO | WO 94/11041 | 5/1994 |
| WO | WO 94/13342 A1 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/29720 A1 | 11/1995 |
| WO | WO 95/31235 A1 | 11/1995 |
| WO | WO 95/35126 A1 | 11/1995 |
| WO | WO 95/35126 A1 | 12/1995 |
| WO | WO 96/30065 A1 | 10/1996 |
| WO | WO 97/10865 A1 | 3/1997 |
| WO | WO 97/13538 A1 | 4/1997 |
| WO | WO 97/48430 A1 | 12/1997 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 99/59658 A1 | 11/1999 |
| WO | WO 00/07539 A1 | 2/2000 |
| WO | WO 00/13723 A2 | 3/2000 |
| WO | WO 00/24441 A1 | 5/2000 |
| WO | WO 00/35516 | 6/2000 |
| WO | WO 00/50107 A1 | 8/2000 |
| WO | 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/77384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | WO 02/074361 A2 | 9/2002 |
| WO | WO 03/013632 A2 | 2/2003 |
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 | 11/2003 |
| WO | WO 03/097133 | 11/2003 |
| WO | WO 03/099358 A2 | 12/2003 |
| WO | WO 2004/007554 A1 | 1/2004 |
| WO | WO 2004/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 A1 | 10/2004 |
| WO | WO 2004/101025 A2 | 11/2004 |
| WO | WO 2004/108194 A1 | 12/2004 |
| WO | WO 2005/004961 A1 | 1/2005 |

(56) References Cited

FOREIGN PATENT DOCUMENTS

| | | |
|---|---|---|
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/122193 A1 | 11/2007 |
| WO | WO 2007/131013 A | 11/2007 |
| WO | WO 2007/138299 A1 | 12/2007 |
| WO | WO 2008/075033 A | 6/2008 |
| WO | WO 2008/093063 A2 | 8/2008 |

OTHER PUBLICATIONS

International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 200608164-0.
International Search Report dated Sep. 5,2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/IB2006/002792.
European Search Report dated Feb. 1, 2006; Application No. 05255298.1.
Great Britain Search Report dated Sep. 22, 2006; Application No. GB0610860.9.
International Search Report dated Aug. 22, 2007; International Application No. PCT/GB2007/001992.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.

(56) References Cited

OTHER PUBLICATIONS

International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.
European Search Report dated Aug. 3, 2011; Application No. 11170040.
Singapore Search Report dated Mar. 15, 2012; Application No. SG 201007017-5.
European Search Report dated Aug. 3, 2011; Application No. 11170040.7.
European Search Report dated Jul. 20, 2011; Application No. 11163762.5.
Australian Search Report dated Feb. 26, 2008; Application No. SG 2006080717.
International Search Report dated Sep. 5, 2005; International Application No. PCT/GB2005/002137.
European Search Report dated Feb. 28, 2011; Application No. 10179733.0.
European Search Report dated Mar. 4, 2011; Application No. 10179736.3.
European Search Report dated Jun. 16, 2011; Application No. 11160134.0.
Australian Search Report dated Dec. 11, 2007; Application No. 200608165-7.
European Search Report dated Apr. 17, 2012; International Application No. 12157660.7.
European Search Report dated Apr. 17, 2012; International Application No. 12157661.5.
European Search Report Dated Oct. 16, 2012; International Application No. 12177505.0.
European Search Report dated Aug. 4, 2011; Application No. 11169691.0.
Great Britain Search Report dated Sep. 29, 2006; Application No. GB0610856.7.
Great Britain Search Report dated Sep. 19, 2006; Application No. GB0610861.7.
Great Britain Search Report dated Nov. 12, 2007; Application No. GB0715457.8.
European Search Report dated Oct. 15, 2013; Application No. 12182553.3.
Great Britain Search Report dated Sep. 25, 2008; Application No. GB0811346.6.
Great Britain Search Report dated Dec. 9, 2013; Application No. GB1310394.0.
Great Britain Search Report dated Dec. 8, 2013; Application No. GB1310389.0.
Great Britain Search Report dated Dec. 9, 2013; Application No. GB1310402.1.
Great Britain Search Report dated Dec. 9, 2013; Application No. GB1310392.4.
Great Britain Search Report dated Dec. 10, 2013; Application No. GB1310393.2.
Great Britain Search Report dated Dec. 10, 2013; Application No. GB1310372.6.

* cited by examiner

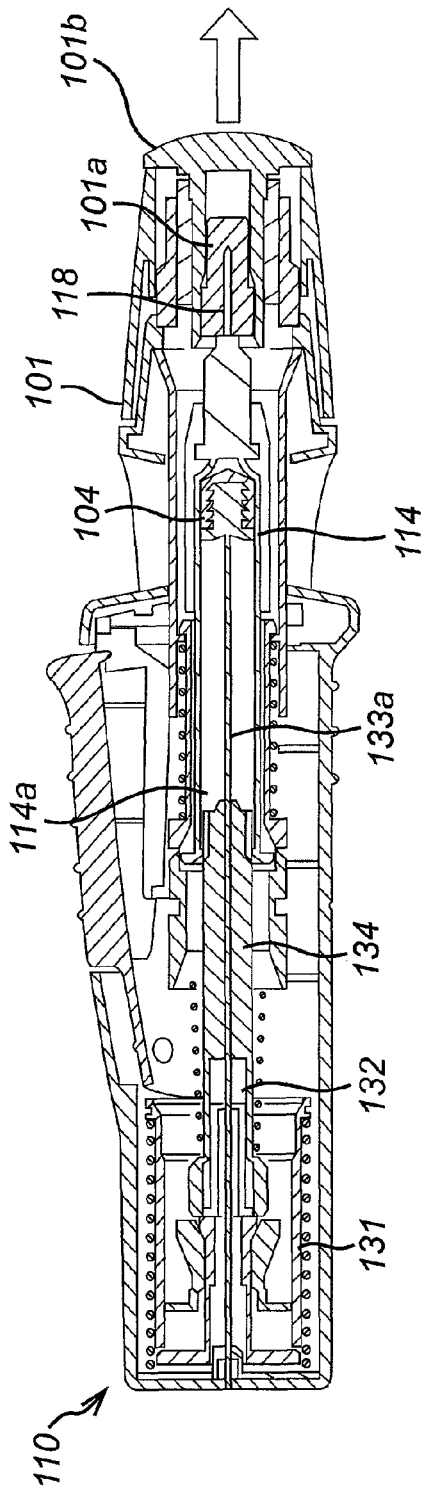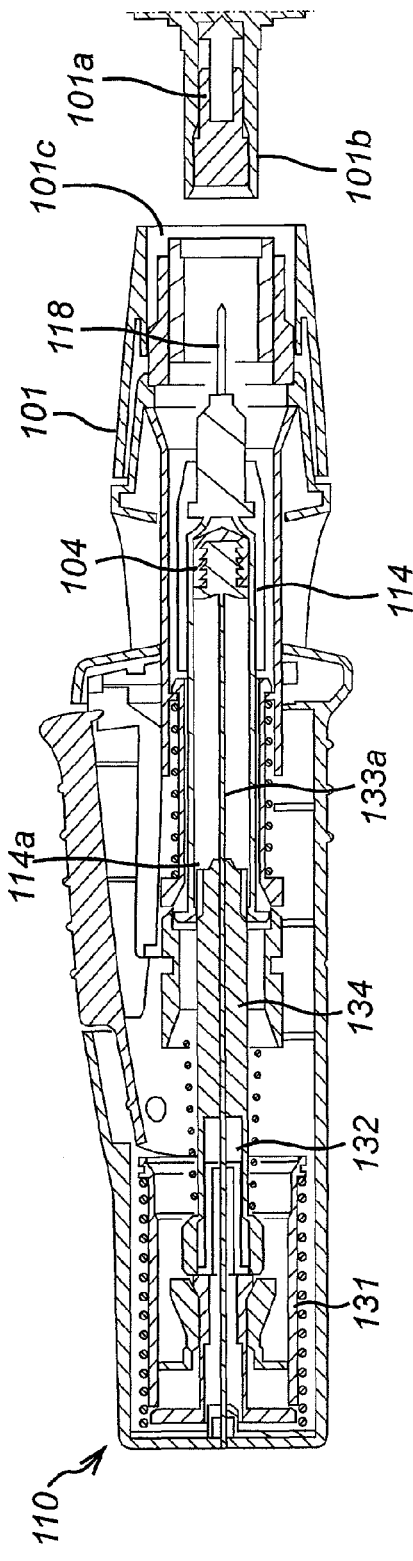

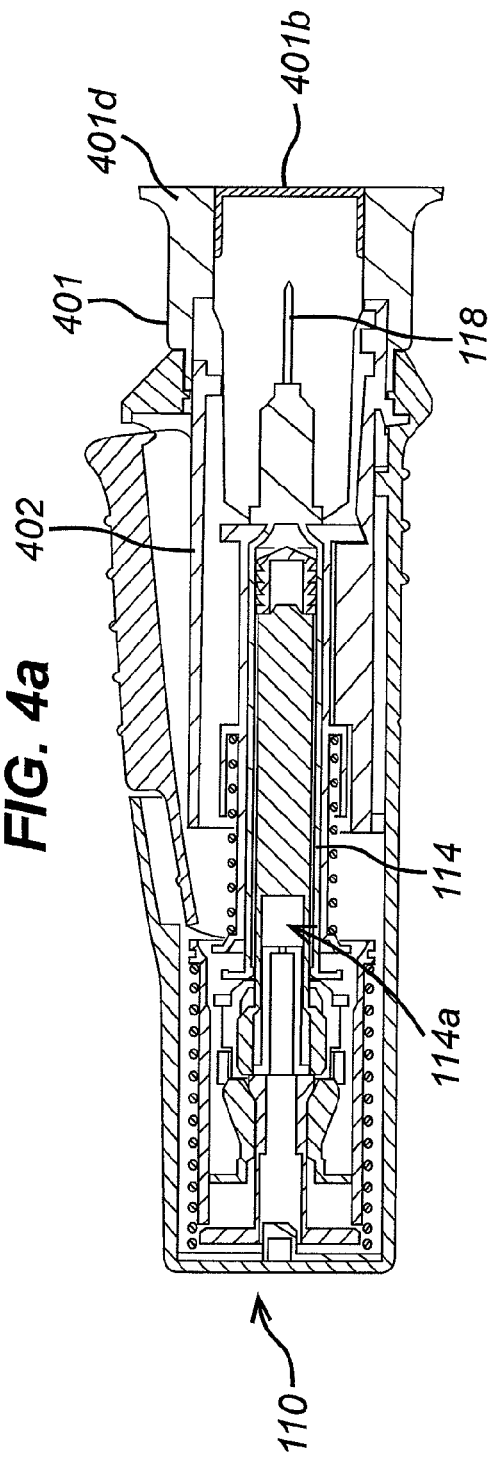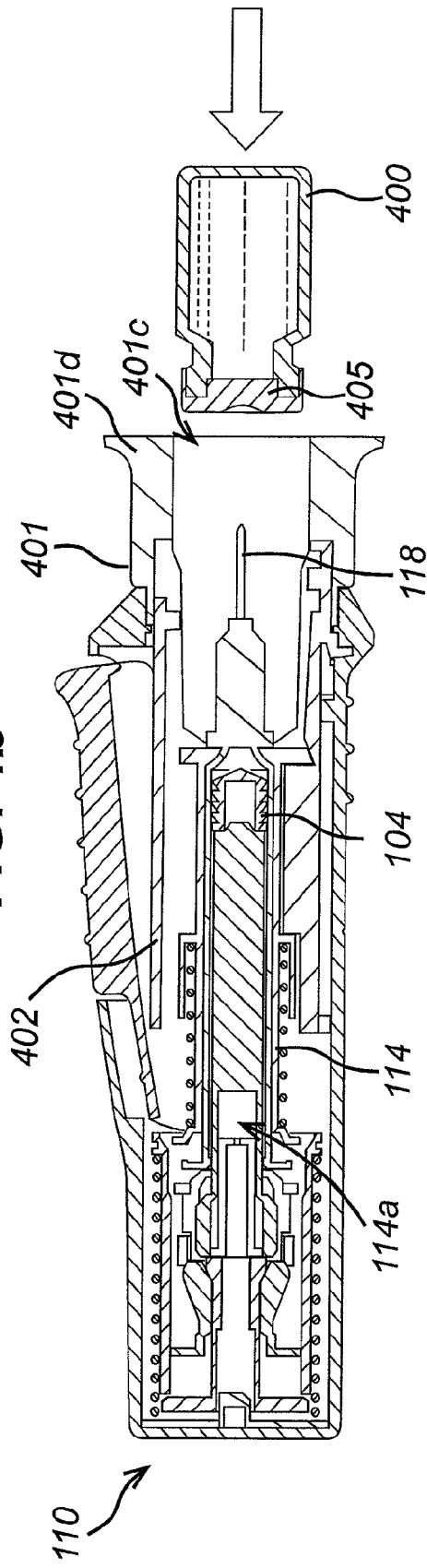

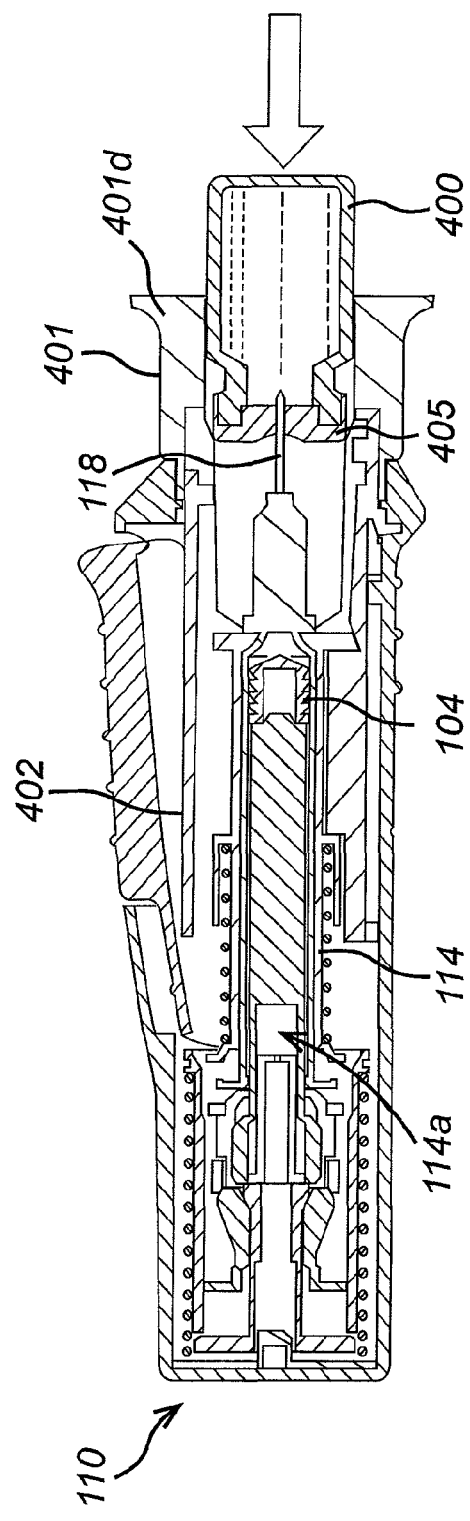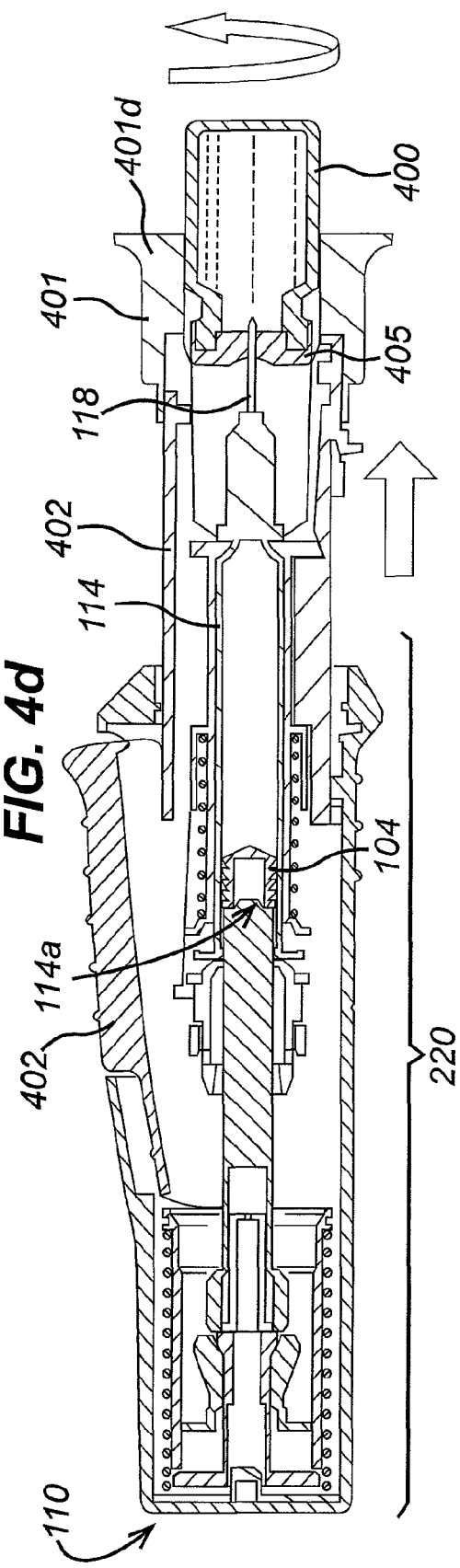

AUTO-INJECTOR WITH FILLING MEANS

FIELD OF THE INVENTION

The present invention relates to an injection device for use with a vial.

BACKGROUND OF THE INVENTION

Subcutaneous drugs can be supplied to patients in a vial for home injection. The current method is for the patient to draw the drug from the vial into a syringe and perform a manual injection. The market is moving towards auto-injectors to carry out home injection. Auto-injectors which are manufactured and assembled including a pre-filled syringe of drug are known, for example from international patent application publication no. 2006/106295, which is incorporated herein by reference. There is currently no easy way for a patient to transfer a subcutaneous drug from a vial into an auto-injector.

SUMMARY OF THE INVENTION

The present invention aims to solve the aforementioned problems.

In a first aspect of the invention, there is provided an injection device comprising:

- a housing adapted to receive a fluid container having a discharge nozzle and a dispensing piston moveable in the fluid container to expel the contents of the fluid container out of the discharge nozzle;
- a drive adapted on activation to act on the fluid container to advance it from a retracted position in which the discharge nozzle is contained within the housing to an extended position in which the discharge nozzle extends from the housing and act on the dispensing piston to expel the contents of the fluid container out of the discharge nozzle;

characterised by:

- a connector adapted to receive a vial containing fluid and connect it to the discharge nozzle; and
- means to move the dispensing piston relative to the fluid container from a first position in which the dispensing piston is located in the fluid container adjacent the discharge nozzle to a second position in which the dispensing piston has been drawn away from the discharge nozzle, thereby drawing fluid from the vial into the fluid container.

The provision of means to move the dispensing piston relative to the fluid container permits the syringe in the injection device to be filled from a standard vial which greatly facilitates home use of the injection device for drugs that are contained in vials.

In one embodiment of the present invention, the injection device comprises a drive sub-assembly including the drive and dispensing piston and a dispensing sub-assembly including the connector and fluid container, wherein the dispensing piston is connected to the drive,
wherein the drive sub-assembly and dispensing sub-assembly are adapted to slide relative to each other,
wherein the drive sub-assembly and dispensing sub-assembly are arranged such that when they are pulled apart from each other, the dispensing piston moves from its first position into its second position thereby transferring fluid from the vial into the fluid container.

Preferably, the dispensing sub-assembly is adapted to slide, in part, inside the drive sub-assembly.

Preferably, the dispensing sub-assembly and drive sub-assembly are adapted to rotate relative to each other from an unlocked position in which the dispensing sub-assembly can slide relative to the drive sub-assembly to a locked position in which the dispensing sub-assembly cannot slide relative to the dispensing sub-assembly. In order to facilitate this, locking protrusions may be provided on one of the dispensing sub-assembly or drive sub-assembly and corresponding grooves are provided on the other.

In an alternative embodiment of the invention, the moving means comprises a slider located in the housing in communication with the dispensing piston. The slider may comprise a user-actuatable movement element which protrudes from the housing. The slider may be in magnetic communication with the dispensing piston. Alternatively, the slider may be integrally connected to the dispensing piston.

The receiving means may be a removable cap located over the discharge nozzle on the injection device, wherein the cap has an open end which is adapted to receive the vial, wherein the removable cap is adapted such that removal of the cap from the housing detaches the vial from the discharge nozzle. The removable cap may comprise a removable cover element over the open end, wherein the removable cover element is adapted to be removed prior to insertion of a vial into the open end. Preferably, the removable cover element holds a shield which is located over the discharge nozzle when the removable cover element is in place on the removable cap and which becomes removed from the discharge nozzle when the removable cover element is removed from the removable cap.

On insertion of the vial into the connector, the discharge nozzle pierces a closure element of the vial to form a fluid pathway between the vial and the fluid container.

Preferably, the fluid container is a syringe and the discharge nozzle is a needle.

Preferably, the injection device comprises a release mechanism adapted on activation to release the drive to act on the dispensing piston to move the syringe to its extended position and eject fluid via the discharge nozzle.

In one embodiment of the invention, there is provided a retraction mechanism adapted to move the fluid container from its extended position to its retracted position after the contents of the fluid container has been expelled.

BRIEF DESCRIPTION OF DRAWINGS

One or more embodiments of the present invention are described below with reference to the accompanying drawings, in which:—

FIGS. 3a to 3d show side cross-sectional views of an injection device according to FIG. 1; and FIGS. 4a to 4d show side cross-sectional views of an injection device according to an alternative embodiment of the invention.

DETAILED DESCRIPTION OF THE DRAWINGS

Figure 1:
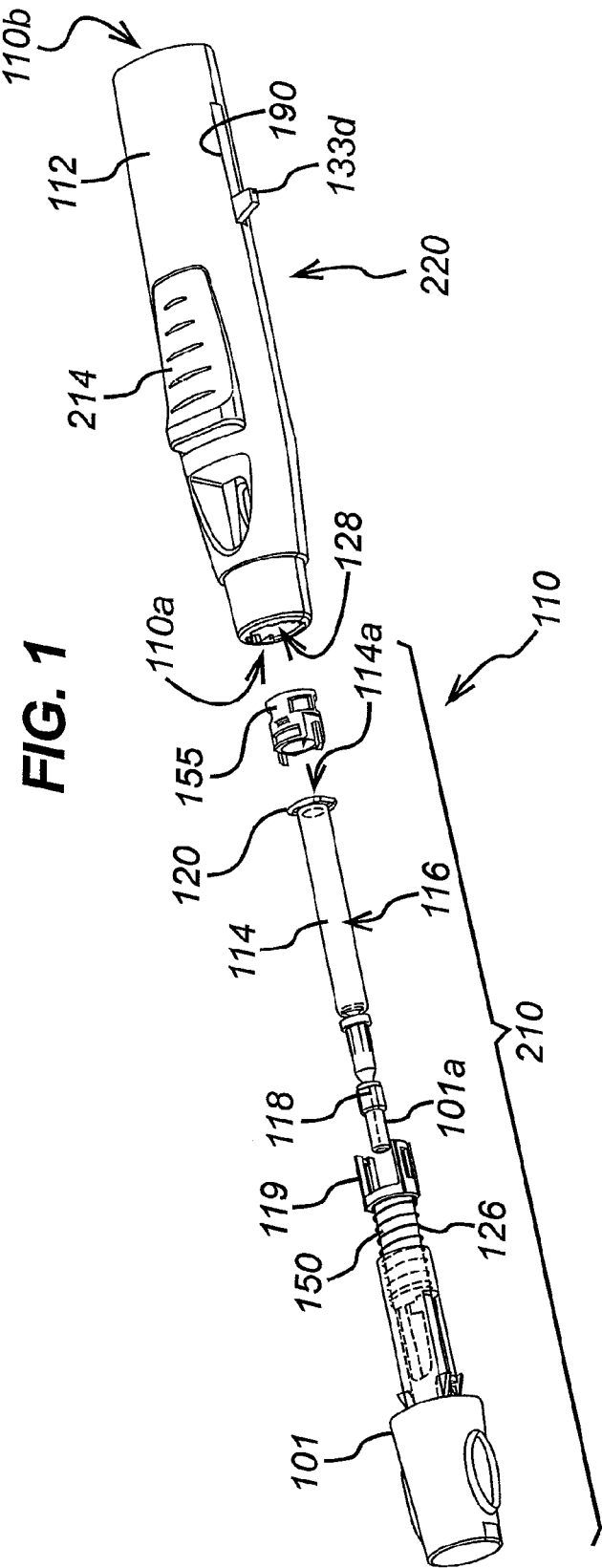
FIG. 1 shows a perspective view of sub-assemblies of the injection device according to one embodiment of the present invention.
Figure 2:
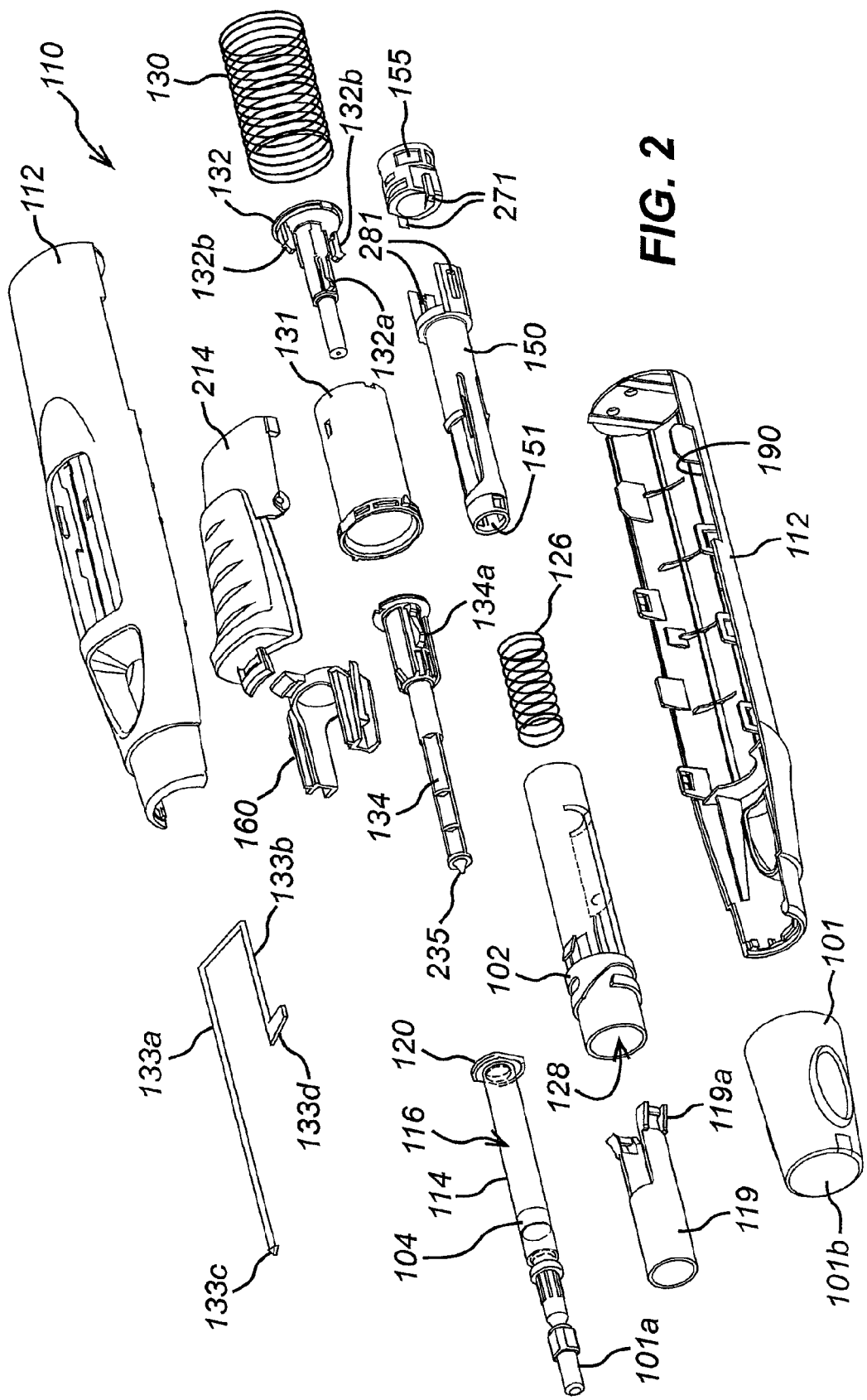
FIG. 2 shows an exploded view of components of the injection device according to embodiment of FIG. 1.
Figure 3C:
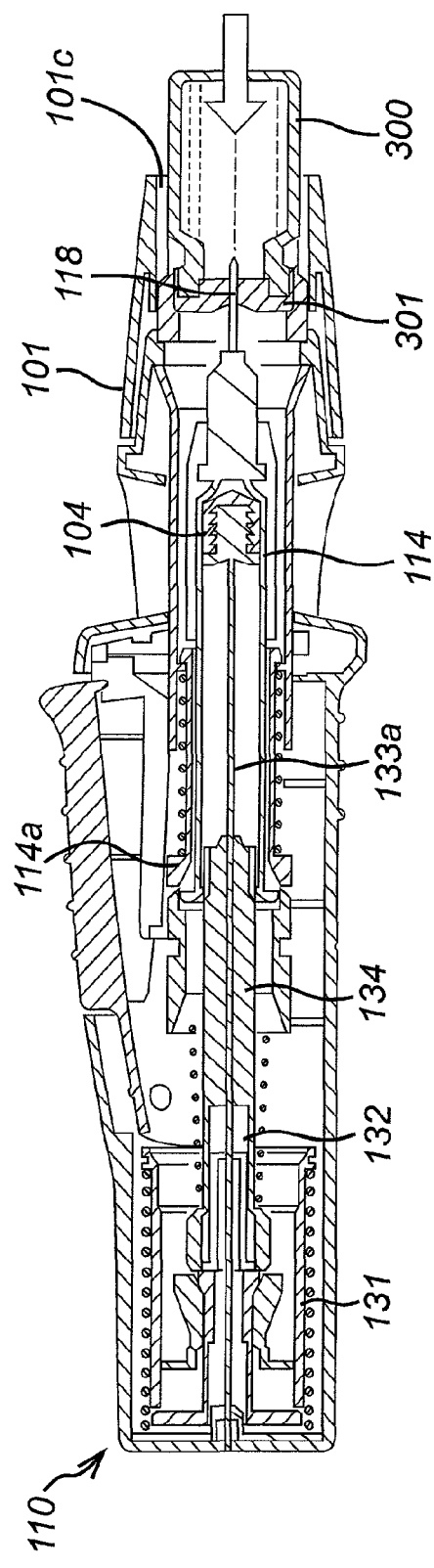
Figure 3D:
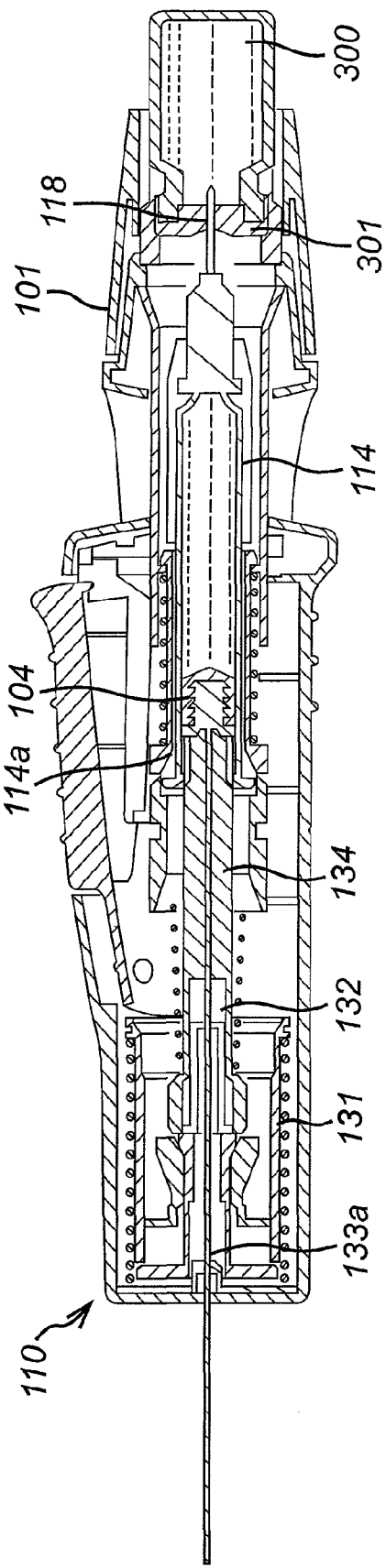

FIGS. 1 and 2 show a delivery device 110 according to the present invention, having a delivery device housing 112 with a proximal end 110a and a distal end 110b. The distal end 110a of the housing 112 has an exit aperture 128, through which the end of a sleeve 119 can emerge.

The delivery device 110 is assembled from two sub-assemblies as shown in FIG. 1. A delivery sub-assembly 210 comprises nose portion 102, a syringe carrier 150, an interchangeable release element 155, sleeve 119 and spring 126, as well as an end-cap 101. The nose portion 102 surrounds and supports the syringe carrier 150 and connects to the 101 cap by a screw and twist connection.

A drive sub-assembly 220 comprises the housing 112 and drive elements and actuators of the injection device 110 as will be discussed below. Upon assembly of the two sub-assemblies 220, 210 to form the injection device 110, the drive assembly 220 is able to actuate the syringe 114 held by the delivery sub-assembly 210. After actuation, the two sub-assemblies can be separated and the drive elements and actuators of the drive assembly 220 reset for further use.

The housing 112 is adapted to receive a hypodermic syringe 114 of conventional type, including a syringe body 116 defining a reservoir and terminating at one end in a hypodermic needle 118 and at the other in a flange 120. The syringe body 116 is of substantially constant diameter along the length of the reservoir, and is of significantly smaller diameter close to the end of the syringe 114 which terminates in the hypodermic needle. A drive coupling 134 acts through the bung of the syringe 114 to discharge the contents of the syringe 114 through the needle 118. This drive coupling 134 constrains a drug to be administered via a plunger 104 within the reservoir defined by syringe body and also permits the drug to be loaded into the syringe 114. Whilst the syringe 114 illustrated is of hypodermic type, this need not necessarily be so. Transcutaneous or ballistic dermal and subcutaneous syringes may also be used with the injection device of the present invention.

As illustrated, the syringe 114 is housed in the syringe carrier 150 within the delivery sub-assembly 210. The syringe carrier 150 has a proximal end 151 through which the needle 118 of the syringe protrudes. The return spring 126, via the return spring support 160 and the syringe carrier 150 biases the syringe 114 from an extended position in which the needle 118 extends from the aperture 128 in the housing 112 to a retracted position in which the needle 118 is contained within the housing 112.

The syringe carrier 150 comprises a sheath (not shown) into which the syringe 114 can be inserted from a distal end 170. The syringe 114 is provided with a boot 101a over the needle 118. If the syringe were to fail or break, the sheath, which surrounds the syringe 114 along its length, would contain the broken pieces of syringe and reduce the likelihood of them from escaping from the injection device 110.

The boot 101a protects the needle 118 and seals it against contamination prior to removal of the boot 101a. The boot 101a is gripped, after the syringe 118 has been inserted into delivery sub-assembly 210, by cap 101, which is removably located on the housing 112 over the exit aperture 128. The boot 101a is gripped in cap 101 by cover element 101b which is removable from the cap 101 so that the boot 101a is also removed, thereby exposing a port 101c, which is an opening formed in an open end of the cap 101.

The housing 112 of the drive assembly 220 also includes an actuator 214, and a drive which here takes the form of a compression drive spring 130. Drive from the drive spring 130 is transmitted via a multi-component drive to the piston of the syringe 114 to advance the syringe 114 from its retracted position to its extended position and discharge its contents through the needle 118. The drive accomplishes this task by acting directly on the drug and the syringe 114. Static friction between the drive coupling 134 and the syringe body 116 initially ensures that they advance together, until the return spring 126 bottoms out or the syringe body 116 meets some other obstruction (not shown) that retards its motion.

The multi-component drive between the drive spring 130 and the syringe 114 consists of three principal components. A drive sleeve 131 takes drive from the drive spring 130 and transmits it to a drive element 132. This in turn transmits drive to the drive coupling 134 already mentioned.

The drive element 132 includes a user-actuatable syringe loading element 133 which engages with the drive coupling 134 internally via locking elements 133c and extends via a first arm 133a through the drive element 132. On assembly, in an unloaded position, a distal end 235 of the drive coupling 134 sits against a plunger 104 within the syringe 114 at its distal end adjacent the connection to the needle 118. The first arm 133a is connected at its proximal end to a second arm 133b which comprises a user-actuable protrusion 133d. On assembly, the user-actuatable protrusion 133d extends out of the housing via slot 190. A further slot (not shown) on the proximal end of the housing 112 permits the first and second arms 133a, 133b to extend out of the housing 112 when the syringe loading element 133 and plunger 104 is moved by sliding user-actuatable protrusion 133a proximally to a proximal position, adjacent the open end 114a of the syringe 114. In the loaded position, the drive element 132 becomes locked to drive coupling 134 via latching arms 132a, 134a on the drive element 132 and drive coupling 134. Thus, the drive coupling 134 can now move with the drive element 132 and drive sleeve 131 on release of the drive spring 130. In an alternative embodiment of the invention, the syringe loading element 133 may be connected directly to the plunger through a bore in the first arm 133a and the drive coupling 134 may be in a proximal position at the open end 114a of the syringe 114. The syringe loading element 133 is then actuated to slide the plunger 104 towards a proximal position at the open end 114a of the syringe 114 adjacent the syringe coupling 134.

The actuator 214, in the form of a trigger, is provided on the housing 112 remote from the exit aperture 128. The trigger, when operated, serves to decouple the drive sleeve 131 from the housing 112, allowing it to move relative to the housing 112 under the influence of the drive spring 130. The operation of the device is then as follows. The actuator 214 is prevented from being actuated by sliding sleeve 119 and sliding sleeve locking element 119a when the sliding sleeve 119 is in its most distal position extending out of the exit aperture 128. When the distal end of the sliding sleeve is placed against tissue or pushed into the exit aperture, the locking element 119a no longer acts on the actuator 214 and the actuator can be actuated.

The actuator is then depressed and the drive spring 130 is released. The drive spring 130 moves the drive sleeve 131, the drive sleeve 131 moves the drive element 132 and the drive element 132 moves the drive coupling 134. The drive coupling 134 moves and, by virtue of static friction and hydrostatic forces acting through the drug to be administered, moves the syringe body 114 against the action of the return spring 126. The syringe body 114 moves the syringe carrier 150, which in turn moves the return spring support 160 and compresses the return spring 126. The hypodermic needle 118 emerges from the exit aperture 128 of the housing 112. This continues until the return spring 126 bottoms out or the syringe body 116 meets some other obstruction (not shown) that retards its motion. Because the static friction between the drive coupling 134 and the syringe body 116 and the hydrostatic forces acting through the drug to be administered are not sufficient to resist the full drive force developed by the drive spring 130, at this point the drive coupling 134 begins to move within the syringe body 116 and the drug begins to be discharged. Dynamic friction between the drive coupling 134 and the syringe body 116 and hydrostatic and hydrodynamic forces now acting through the drug to be administered are, however, sufficient to retain the return spring 126 in its compressed state, so the hypodermic needle 118 remains extended.

Before the drive coupling 134 reaches the end of its travel within the syringe body 116, so before the contents of the syringe have fully discharged, flexible latch arms 134b linking the first and drive couplings 132, 134 reach an interchangeable release element 155 connected to the distal end of the syringe carrier 150.

The interchangeable release element 155 is essentially a constriction which moves the flexible latch arms 132b to a position so that they no longer couple the drive element 132 to the drive coupling 134. Once this happens, the drive element 132 acts no longer on the drive coupling 134, allowing the drive element 132 to move relative to the drive coupling 134. Consequently, the drive coupling 134 continues to move within the syringe body 116 and the drug continues to be discharged. Thus, the return spring 126 remains compressed and the hypodermic needle remains extended.

After a time, the drive coupling 134 completes its travel within the syringe body 116 and can go no further. At this point, the contents of the syringe 114 are completely discharged and the force exerted by the drive spring 130 acts to retain the drive coupling 134 in its terminal position, allowing the drive element 132 to continue its movement.

Flexible latch arms linking the drive sleeve 131 with the drive element 132 reach another constriction within the housing 112. The constriction moves the flexible latch arms so that they no longer couple the drive sleeve 131 to the drive element 132. Once this happens, the drive sleeve 131 acts no longer on the drive element 132, allowing them to move relative each other. At this point, the forces developed by the drive spring 130 are no longer being transmitted to the syringe 114. The only force acting on the syringe will be the return force from the return spring 126 which acts on the end of the syringe 114 nearest to the needle 118 via the return spring support 160 and the syringe carrier 150. Consequently, the syringe is returned to its retracted position and the injection cycle is complete.

FIGS. 3a to 3d show one embodiment of the injection device 110 and the steps by which it is loaded with fluid from a vial 300 prior to injection. The vial 300 is of standard size and comprises a closure element 301 which seals the vial. The closure element 301 may be in the form of a flexible membrane which can be pierced by the needle 118. The port 101c in the cap 101 is sized and dimensioned to receive the vial 300 and support it whilst fluid is extracted from the vial into syringe 114. The process for doing this is as follows.

As shown in FIG. 3b, the closure element 101b is removed from the cap 101 whilst the cap 101 remains in place on the housing 112. This removes the boot 101a from the needle 118 and opens the port 101c, in which the needle 118 is exposed.

The vial 300 is inserted into the port 101c end first, i.e. the end which includes the closure element 301. As the vial 300 is inserted, the needle pierces the closure element 301 and extends into the vial 300 so that its end point resides in the fluid contained within the vial 300. Preferably, the injection device 110 should now be positioned so that its longitudinal axis extends vertically with the vial 300 located nearest the ground. Gravity acts on the fluid in the vial 300 to keep it in the bottom of the vial, so that the fluid can be extracted.

The user can now operate the syringe loading element 133 by sliding the protrusion 133d towards the proximal end of the injection device 110. This causes the plunger 104 in the syringe 114 to move from its unloaded position towards the proximal end of the syringe 114 into its loaded position and extract fluid from the vial 300 into the syringe 114 via a reduction of pressure in the syringe 114. When the syringe loading element 133 has reached its loaded position, i.e. at the most proximal end of the slot 190, the syringe 114 has been loaded with fluid from the vial 300. The vial 300 can now be removed from the injection device 110 by removing the cap 101 so that the injection device 110 is ready for use, by placing the distal end of the sliding 119 sleeve against tissue and activating the actuator 214.

FIGS. 4a to 4d show an alternative embodiment of the injection device 110 and the steps by which it is loaded with fluid from a vial 400 prior to injection. The structure of the injection device 110 of this alternative embodiment is the same as for the embodiment depicted in FIGS. 1 and 2, except for the differences explained below. As in the embodiment of FIGS. 3a to 3d, the vial 400 is of standard size and comprises a closure element 405 which seals the vial 400. The closure element 405 may be in the form of a flexible membrane which can be pierced by the needle 118. In this alternative embodiment, the cap 401 of the delivery sub-assembly 210, comprises a cover element 401b and flange 401d at its distal end. The cap 401 is also connected to nose portion 402 of the delivery sub-assembly 210 which is slidable and rotatable into and out of the housing 112 between an unloaded and loaded position. In its extended loaded position, the nose portion 402 can be rotated to lock its position relative to the housing 112. As in the embodiment described in FIGS. 1 and 2, the nose portion 402 supports the syringe 114 which moves with the syringe portion relative to the drive coupling 134, which in this alternative embodiment, is fixed to the drive element 132. In this alternative embodiment, there is no syringe loading element. A port 401c in the cap 101 is sized and dimensioned to receive the vial 400 and support it whilst fluid is extracted from the vial into syringe 114. The process for doing this is as follows.

As shown in FIG. 4b, the closure element 401b is removed from the cap 401 whilst the cap 401 remains in place on the housing 112. This removes the boot 101a from the needle 118 and opens the port 401c, in which the needle 118 is exposed.

The vial 400 is inserted into the port 401c end first, i.e. the end which includes the closure element 401. As the vial 400 is inserted, the needle 118 pierces the closure element 401 and extends into the vial 400 so that its end point resides in the fluid contained within the vial 400. Preferably, the injection device 110 should now be positioned so that its longitudinal axis extends vertically with the vial 300 located nearest the ground. Gravity acts on the fluid in the vial 400 to keep it in the bottom of the vial, so that the fluid can be extracted.

The user can now slide the delivery sub-assembly 210 relative to the drive sub-assembly 220 by, for example, pulling on the flange 401d to cause the cap 401 and nose portion 402, including the syringe 114, to extend away from the distal end of the drive sub-assembly 220. This causes the plunger 104, held by the drive coupling 134, in the syringe 114 to move from its unloaded position towards the proximal open end 114a of the syringe 114 into its loaded position and extract fluid from the vial 400 into the syringe 114 via a reduction of pressure in the syringe 114. When the delivery sub-assembly 210 is fully extended from the drive sub-assembly 220, the cap 401 and nose portion 402 can be rotated to lock and prevent further longitudinal movement of the delivery sub-assembly 210 relative to the drive sub-assembly 220. The syringe 114 has now been loaded with fluid from the vial 400. The vial 400 can now be removed from the injection device 110 by removing the cap 101, for example by further rotation, so that the injection device 110 is ready for use, by placing the distal end of the sliding 119 sleeve against tissue and activating the actuator 214.

It will of course be understood that the present invention has been described above purely by way of example and modifications of detail can be made within the scope of the invention.

What is claimed is:

1. An injection device comprising:
    a housing adapted to receive a fluid container, the fluid container having a discharge nozzle, and a dispensing piston moveable in the fluid container to expel the contents of the fluid container out of the discharge nozzle;
    a drive adapted on activation to act on the fluid container to advance it from a retracted position in which the discharge nozzle is contained within the housing to an extended position in which the discharge nozzle extends from the housing and act on the dispensing piston to expel the contents of the fluid container out of the discharge nozzle;
    a connector adapted to receive a vial containing fluid and connect it to the discharge nozzle; and
    means to move the dispensing piston relative to the fluid container from a first position in which the dispensing piston is located in the fluid container adjacent the discharge nozzle to a second position in which the dispensing piston has been drawn away from the discharge nozzle, thereby drawing fluid from the vial into the fluid container.

2. The injection device of claim 1, comprising a drive sub-assembly including the drive and the dispensing piston and a dispensing sub-assembly including the connector and the fluid container,
    wherein the dispensing piston is connected to the drive,
    wherein the drive sub-assembly and dispensing sub-assembly are adapted to slide relative to each other,
    wherein the drive sub-assembly and dispensing sub-assembly are arranged such that when they are pulled apart from each other, the dispensing piston moves from its first position into its second position thereby transferring fluid from the vial into the fluid container.

3. The injection device of claim 2, wherein the dispensing sub-assembly is adapted to slide, in part, inside the drive sub-assembly.

4. The injection device of claim 2 or claim 3, wherein the dispensing sub-assembly and drive sub-assembly are adapted to rotate relative to each other from an unlocked position in which the dispensing sub-assembly can slide relative to the drive subassembly to a locked position in which the dispensing sub-assembly cannot slide relative to the dispensing sub-assembly.

5. The injection device of claim 1, wherein the moving means comprises a slider located in the housing in communication with the dispensing piston.

6. The injection device of claim 5, wherein the slider comprises a user-actuatable movement element which protrudes from the housing.

7. The injection device of claim 5 or claim 6, wherein the slider is in magnetic communication with the dispensing piston.

8. The injection device of claim 5 or claim 6, wherein the slider is integrally connected to the dispensing piston.

9. The injection device of claim 1, wherein the connector is a removable cap located over the discharge nozzle on the injection device, wherein the cap has an open end which is adapted to receive the vial, wherein the removable cap is adapted such that removal of the cap from the housing detaches the vial from the discharge nozzle.

10. The injection device of claim 9, wherein the removable cap comprises a removable cover element over the open end, wherein the removable cover element is adapted to be removed prior to insertion of a vial into the open end.

11. The injection device of claim 10, wherein the removable cover element holds a shield which is located over the discharge nozzle when the removable cover element is in place on the removable cap and which removed from the discharge nozzle when the removable cover element is removed from the removable cap.

12. The device of claim 1, wherein, on insertion of the vial into the connector, the discharge nozzle pierces a closure element of the vial to form a fluid pathway between the vial and the fluid container.

13. The injection device of claim 1, wherein the fluid container is a syringe and the discharge nozzle is a needle.

14. The injection device of claim 1, comprising a release mechanism adapted on activation to release the drive to act on the dispensing piston to move the syringe to its extended position and eject fluid via the discharge nozzle.

15. The injection device of claim 1, comprising a retraction mechanism adapted to move the fluid container from its extended position to its retracted position after the contents of the fluid container has been expelled.

\* \* \* \* \*